(12) United States Patent
Wen et al.

(10) Patent No.: US 10,959,998 B2
(45) Date of Patent: Mar. 30, 2021

(54) PHARMACEUTICAL USE AND PHARMACEUTICAL COMPOSITION OF PYRROLOQUINOLINE QUININE, ITS DERIVATIVES AND/OR ITS SALTS

(71) Applicant: NANJING SHUPENG LIFESCIENCE CO., LTD, Jiangsu (CN)

(72) Inventors: Chuanjun Wen, Jiangsu (CN); Fenyong Sun, Jiangsu (CN)

(73) Assignee: NANJING SHUPENG LIFESCIENCE CO., LTD., Jiangsu (CN)

( * ) Notice: Subject to any disclaimer, the term of this patent is extended or adjusted under 35 U.S.C. 154(b) by 135 days.

(21) Appl. No.: 15/569,781

(22) PCT Filed: Apr. 20, 2016

(86) PCT No.: PCT/CN2016/079709
§ 371 (c)(1),
(2) Date: Oct. 27, 2017

(87) PCT Pub. No.: WO2016/173435
PCT Pub. Date: Nov. 3, 2016

(65) Prior Publication Data
US 2018/0140596 A1 May 24, 2018

(30) Foreign Application Priority Data

Apr. 27, 2015 (CN) .......................... 201510206583.8

(51) Int. Cl.
*A61K 31/4745* (2006.01)
*A61K 31/223* (2006.01)
*A61P 15/00* (2006.01)
*A61K 45/06* (2006.01)
*C07D 471/04* (2006.01)

(52) U.S. Cl.
CPC ........ *A61K 31/4745* (2013.01); *A61K 31/223* (2013.01); *A61K 45/06* (2013.01); *A61P 15/00* (2018.01); *C07D 471/04* (2013.01)

(58) Field of Classification Search
CPC .... A61K 31/223; A61K 31/4745; A61P 15/00
See application file for complete search history.

(56) References Cited

U.S. PATENT DOCUMENTS 8,637,573 B2 * 1/2014 Parasassi ............. A61K 31/198
514/562
2016/0075700 A1 3/2016 Ikemoto

OTHER PUBLICATIONS

STN registry database 72909-34-3 (entered STN Nov. 16, 1984) (Year: 1984).*
Durak et al. (The Journal of Obstetrics and Gynaecology Research, 39, 1253-1258, 2013) (Year: 2013).*
Rucker et al. (Alternative Medicine Review, 14, 268-277, 2009) (Year: 2009).*
The Telegraph (The world's fattest countries: how do you compare? Jun. 41, 2012, https://www.telegraph.co.uk/news/earth/earthnews/9345086/The-worlds-fattest-countries-how-do-you-compare.html) (Year: 2012).*
Danilyants et al. (The Center for Innovative GYN Care, Learn the Difference Between Adenomyosis and Endometriosis, Apr. 15, 2015, https://innovativegyn.com/learn-the-difference-between-adenomyosis-and-endometriosis/) (Year: 2015).*
1. Bendich A. "The antioxidant role of vitamin C." Advances in Free Radical Biology & Medicine. 1986, 2(2):419-44.
2. Kimura K. Pyrroloquinoline quinone stimulates epithelial cell proliferation by activating epidermal growth factor receptor through redox cycling. Free Radical Biology and Medicine 2012; 53: 1239-1251.
3. Akagawa M. Sci Rep. 2016 27;6:26723.
4. Aizenman,E. Interaction of the putative essential nutrient pyrroloquline quinine with the N-methyl-D-aspartate receptor redox modulatory site. J. Neurosci. 1992.12, 2362-2369.
5. Hiraku Y and Kawanishi S. NADH-mediated DNA damage induced by a new coenzyme, pyrroloquinoline quinine, in the presence of copper(II) ion. FEBS Lett. 1996 16; 393(2-3):317-20.
6. Takada M. Pyrroloquinoline quinone, a novel protein tyrosine phosphatase 1B inhibitor, activates insulin signaling in C2C12 myotubes and improves impaired glucose tolerance in diabetic KK-A(y) mice. Biochem Biophys Res Commun. 2012 16; 428(2):315-20.
7. Sasakura H. Lifespan extension by peroxidase and dual oxidase-mediated ROS signaling through pyrroloquinoline quinone in C. elegans. J Cell Sci. 2017 1; 130(15): 2631-2643.
8. Min Z. Pyrroloquinoline Quinone Induces Cancer Cell Apoptosis via Mitochondrial-Dependent Pathway and Down-Regulating Cellular Bcl-2 Protein Expression. Journal of Cancer 2014; 5(7): 609-624.

* cited by examiner

*Primary Examiner* — Barbara P Badio
(74) *Attorney, Agent, or Firm* — Frank Gao, Esq.

(57) ABSTRACT

The present invention relates to the use of pyrroloquinoline quinine (PQQ), its derivatives and/or salts for the preparation of drugs for the treatment and/or prevention of endometriosis including adenomyosis, chocolate cyst of ovary, deeply infiltrating endometriosis and other type of endometriosis. In addition, the present invention relates to the use of PQQ in combination with one or more the following antioxidants: N-Acetyl-L-cysteine (NAC), resveratrol, epigallocatechin gallate, vitamin E or vitamin C for the preparation of drugs for inhibiting the proliferation, oxidative stress status, invasion and migration of endometrial stromal cell. The use of PQQ in combination with NAC shows a synergistic effect on inhibiting cell proliferation: significantly inhibiting the proliferation of endometrial stromal cell in vitro; significantly reducing the damaged size of tissue caused by endometriosis in vivo; significantly reducing the infiltration of endometrial stroma and glands; significantly reducing the dose of NAC as well. PQQ is beneficial for fertility, and increases the chances of getting pregnant. PQQ alone or PQQ in combination with NAC generally shows no side effects and will not interfere with pregnancy.

3 Claims, 5 Drawing Sheets

PHARMACEUTICAL USE AND PHARMACEUTICAL COMPOSITION OF PYRROLOQUINOLINE QUININE, ITS DERIVATIVES AND/OR ITS SALTS

This application is a national stage application of PCT application PCT/CN2016/079709 filed on Apr. 20, 2016, which is hereby incorporated by reference herein in its entirety.

This application claims priority of No. 201510206583.8 of the Chinese patent applications filed by the same applicant and inventor on Apr. 27, 2015.

FIELD OF THE INVENTION

The invention relates to new pharmaceutical use and pharmaceutical composition of pyrroloquinoline quinine, its derivatives and/or its salts, and more specifically relates to use of pyrroloquinoline quinine (PQQ), its derivatives and/or its salts for the preparation of drugs for the treatment and/or prevention of endometriosis.

BACKGROUND ART

Endometriosis (EM) is a disease (or a series of lesions and symptoms) caused by the growth of viable endometrial tissue outside the uterine cavity, including adenomyosis, chocolate cyst of ovary, deeply infiltrating endometriosis, and is an estrogen dependant disease. The common clinical symptoms include dysmenorrhea, infertility, chronic pelvic pain, algopareunia, pelvic mass, acute abdomen and even canceration. EM is a common disease in women of productive ages with prevalence rates of up to 10%-15%. In recent years, the prevalence of EM continues to show a significant upward trend. Nearly a half of the EM patients are infertile. What is even worse is that though EM is a benign disease, but ectopic endometrial tissues exhibit malignant behaviour like infiltration, diffusion and distant metastasis. The disease can invade many parts of the body (such as nasal cavity, lung, kidney, ureter, bladder, intestine, and so on) and therefore it is also called "benign cancer", which seriously affect the patient's health in both physical and mental aspects.

It is generally accepted that the backward flow of menstrual blood and endometrial implantation are the main causes of endometriosis. For endometrial cells to successfully backward flow, implant and grow outside of the uterine cavity, the following four basic conditions must be met: (1) Endometrial cells must enter into the abdominal cavity through the fallopian tube; (2) Endometrial cells in the fragment of backward-flowing menstrual blood must be viable; (3) Endometrial cells must be able to implant on the pelvic tissues and organs; (4) The distribution of endometriosis in pelvic anatomy must be consistent with the planting principle of exfoliated endometrial cells. Therefore, the biological behaviour similar to tumor metastasis such as metastasis, implantation and growth of ectopic endometrium may be crucial in the pathogenesis of endometriosis.

Currently, the therapy method for EM consists of two major classes, i.e. surgical and drug treatment. Routine surgical treatment of EM is a conservative treatment method, which removes the endometriosis lesions, while retains uterus and normal ovarian tissue. The recurrence rate of EM after the surgery is very high. Radical surgery has a good therapeutic effect, but need to remove the uterus and bilateral accessory, which makes women completely lost the endocrine function of ovarian function and fertility, so it is not suitable for patients of reproductive age. The commonly used drugs for EM are composed of four classes: progesterone, testosterone derivatives, danazol and nemestran, gonadotropin-releasing hormone agonis (GnRH-a). These drugs achieve the treatment goals mainly by regulating the hypothalamic pituitary ovarian axis, directly or indirectly interfering with estrogen level and creating pseudo pregnant or pseudo menopause. So these drugs can not be used for a long time, which makes it harder to get pregnant during drug treatment. Moreover, during drug treatment estrogen in the patient's body is still maintained at a certain level and performs physiological functions to a certain extent. Since the deeply infiltrating ectopic tissue is independent on the estrogen in peripheral blood, which can produce estrogen by itself, the ectopic tissue still exists during the drug treatment. Once these drugs are ceased, ectopic tissue is very likely to reappear. According to statistics, the recurrence rate of EM after drug treatment is about 25%-67%.

Previous study showed that the increase in the cell proliferation is associated with the elevated level of oxygen free radicals, and oxidative stress plays an important role in the formation and development of EM (Murphy et. al., Semin Reprod Endocrinol. 1998; 16:263-73). Activated macrophages in the peritoneal cavity can than areas with high oxidative stress, where lipid peroxides and their degradation products are included (Agarwal et. al., Curr Opin Obstet Gynecol. 2006; 18:325-32). The high oxidative stress state will further lead to inflammatory reaction, promote the secretion of inflammation and transforming growth factors, releasing them into the peritoneal fluid of the patients (Van Langendonckt et. al., Fertile Steril. 2002; 77:861-70). These factors, in turn, can constantly drive the implantation and growth of endometrial tissue in the abdominal cavity. (Santanam et. al., Ann N Y Acad Sci. 2002; 955:183-98).

It has been reported that the production of $O_2^-$ in stromal endometriotic cells is significantly higher than that in stromal control cells (Ngǒ et. al., Am J Pathol. 2009 July; 175(1):225-34) EM tissue, the increase in the concentration of $O_2^-$ in turn promotes the proliferation of stromal endometriotic cells by activating the mTOR/AKT pathway (Leconte et. al., Am J Pathol. 2011 August; 179(2): 880-9).

Studies described above showed that proliferation and invasion of EM cells are positively associated with oxygen free radicals and increased inflammation level. Therefore antioxidation and anti-inflammation may become a new approach for EM treatment (Transl Res. 2013 March; 161 (3): 189-195). The key to achieving this goal is to find out proper antioxidants.

N-acetyl-L-cysteine (NAC) is a precursor of glutathione in vivo and an important antioxidant. Studies in mouse models of endometriosis have demonstrated that NAC at a daily dose of 1.3 g/kg/day can significantly inhibit the growth of EM lesions (C Ngo et. al., Am J Pathol, July 2009; 175(1): 225-34). A recent clinic study showed that after three months of treatment with NAC, cysts sizes within EM patients were reduced significantly, which is better than those treated with hormone (Porpora et. al., Evid Based Complement Alternat Med. 2013; vol 2013: ID 240702). A Chinese patent application (CN 102665707 A) revealed an antioxidant drug called N-acetyl-L-cysteine (NAC) for the treatment of EM, wherein the required NAC dose must be greater than 20 mg/kg body weight/day. The treatment of EM with NAC has obvious deficiency in clinical application. Specifically, the stability of NAC in vivo is not high enough, so its antioxidant capacity is limited and a larger dose is required to ensure its efficacy. Meanwhile, the daily dose of NAC is up to 1.8 grams in human trials. As NAC is an acidic substance, taking NAC at such high dosage may cause digestive symptoms in some patients. Moreover, according to the Pharmacopoeia of the People's Republic of China (2010 edition), NAC as a well-known expectorant has many other adverse reactions, even causes poisoning in some serious cases.

Therefore, it is necessary to seek more stable, safe and powerful antioxidants, which may be used either alone or in combination with small doses of NAC for the treatment of endometriosis.

DETAILED DESCRIPTION OF THE INVENTION

The technical problems to be solved by the present invention include the defects in prior surgical and medical treatment of EM mentioned above, and well-known shortcomings of NAC as a drug used for antioxidant therapy of EM, such as low stability, limited antioxidant ability, high effective dose and a variety of adverse reactions etc.

In order to solve the above problems, the applicants performed a thorough literature research, and found that many antioxidants such as epigallocatechin-3-gallate (EGCG), resveratrol. Ω-3 polyunsaturated fatty acid (omega-3 PUFAs), Vitamin B, E and C etc, all showed certain curative effect on animal model of EM. (Hum Reprod, 2013 January; 28(1):178-88. J Endometr. 2013 Jan. 1; 5(1): 17-26). But so far, there isn't any antioxidant that has been approved as a drug for the treatment of EM. The applicants surmised that the possible reasons include: (1) Similar to NAC, some antioxidants are of poor stability, e.g. vitamin C; (2) Some antioxidants such as omega-3 polyunsaturated fatty acids and vitamin E belong to fat soluble substances, which are difficult to absorb and to reach the therapeutic dose in human body. So the applicants turned their attention to the pyrroloquinoline quinone, derivatives and/or salts thereof that can be expressed in the following structural formula (I).

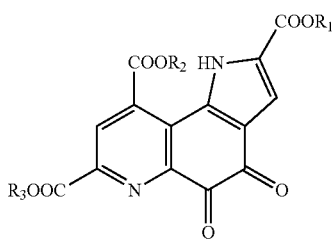

Formula (I)

wherein R1, R2 and R3 are same or not, and are each independently lower alkyl, lower alkenyl, lower alkynyl, alkaryl, aralkyl, benzyl, H, Na and K;

In one embodiment of the present invention, the said lower alkyl group is an alkyl group of 1-4 carbon atoms such as methyl, ethyl, propyl, butyl, and isopropyl group;

In one embodiment of the present invention, the lower alkenyl group is an alkenyl group of 2-4 carbon atoms such as ethylene, propenyl, butenyl and isopropenyl group;

In one embodiment of the present invention, the lower alkyne group is the alkynyl group of 2-4 carbon atoms, such as ethynl, propinyl, butyryl group;

In one embodiment of the present invention, the R1, R2 and R3 are hydrogen atoms;

In one embodiment of the present invention, the R1, R2 and R3 are independently hydrogen atoms or sodium atoms;

In one embodiment of the present invention, PQQ is in the form disodium salt (PQQNa$_2$).

In 1964, PQQ was first found in bacteria as a coenzyme. Subsequent studies have confirmed that PQQ is a water-soluble substance that can act as an electron acceptor or donor to participate in the enzymatic reaction of oxidoreductase. PQQ is widespread in plants and animals, and is widely distributed in human tissues with the highest levels in breast milk. PQQ has a variety of biological functions, which primarily include the following aspects: (1) stimulate the growth of microorganisms, plants and animals; (2) essential nutrients for animal development and reproduction; (3) eliminate excessive free radicals, protect the body from oxidative damage; (4) reduce the expression of inflammatory factors IL-6 and C-reactive protein (CRP) in plasma (Journal of Nutritional Biochemistry 24 (2013) 2076-2084), indicating that PQQ can inhibit inflammation; (5) provide nourishment and protection for neural tissue; (6) improve sleep and cognition. Some scholars proposed to classified PQQ as the 14$^{th}$ vitamin, which has been on sale as a health product in the US and Japan. Because of its unique o-benzoquinone structure, PQQ has a physiological characteristic that other coenzyme does not possess, i.e. the relative stability in chemical properties. This characteristic enables it to be involved in the redox cycle 20,000 times, thus free radical scavenging activity of PQQ is significantly higher than that of vitamin C (Altern Med Rev. 2009 September; 14(3):268-77).

Through numerous studies and experiments, the applicants surprisingly find that pyrroloquinoline quinone, its derivatives and/or salts were quite effective in the treatment and/or prevention of endometriosis.

Through further studies and experiments, the applicants surprisingly find that when combined with other antioxidants such as low dose of NAC etc., pyrroloquinoline quinone, its derivatives and/or salts showed better curative effective in the treatment and/or prevention of endometriosis.

The above mentioned other antioxidants include N-Acetyl-L-cysteine (NAC), resveratrol, epigallocatechin gallate, curcumin, anthocyanidin, vitamin E and vitamin C etc.

The applicant found that in the case of combined use of pyrroloquinoline quinine, derivatives and/or salt thereof and NAC agents, sustained-release and/or gastric protection preparations can be added to the drug combination, in order to reduce gastrointestinal drug reactions through research and experiment.

The present invention provides novel medicinal use of pyrroloquinoline quinone, its derivatives and/or salts, and provides a pharmaceutical composition, whose active ingredients include pyrroloquinoline quinone, derivatives and/or salts thereof. Compared with drugs using N-acetyl cysteine as effective component, the medicine with the pyrroloquinoline quinone, derivatives and/or salt thereof as the active ingredient has the following advantages and progresses:

1) Stable. PQQ has unique o-benzoquinone structure, which makes it stable in chemical property. This characteristic enables it to be involved in the redox cycle 20000 times, thus its free radical scavenging activity is significantly higher than that of vitamin C (Altern Med Rev. 2009 September; 14(3):268-77).

2) Small dosage. In the present medication regimen, the dose of PQQ in the animal experiments is 0.2~1 mg/kg body weight/day, far less than that of NAC in animal experiments (4~1300 mg/kg body weight/day). (The American Journal of Pathology, Vol. 175, No. 1, July 2009, FertilSteril_2010; 94:2905-8.).

3) Safe. The half lethal dose of PQQ in mice was 1000-2000 mg/kg body weight/day. Feeding the mice PQQ at a dose of 100 mg/kg body weight/day for 14 consecutive days did not show any adverse reactions (Regul Toxicol Pharmacol. 2014 October; 70 (1): 107-21).

4) The use of PQQ in combination with low dose of NAC (5~10 mg/kg body weight/day) exhibited evident synergetic effect. This drug combination has a better prospect in the treatment of EM.

The use of pyrroloquinoline quinone, derivatives and/or salts thereof for the preparation of drugs for the treatment of endometriosis has not been reported by now. Moreover, the curative effect of PQQ in treatment of endometriosis is better than that of NAC. Meanwhile, PQQ contributes to fertility and increases the chances of getting pregnancy, which is unavailable for the existing drugs used clinically for the treatment of EM.

In first aspect, the present invention relates to the use of pyrroloquinoline quinone, derivatives and/or salts thereof in the preparation of drugs for the treatment and/or prevention of endometriosis.

In second aspect, the present invention relates to use in first aspect thereof characterized in that the said endometriosis is adenomyosis.

In third aspect, the present invention relates to use in first aspect thereof characterized in that the said endometriosis is chocolate cyst of ovary.

In fourth aspect, the present invention relates to use in first aspect thereof characterized in that the said endometriosis is deeply infiltrating endometriosis.

The fifth aspect of the present invention relates to the use of pyrroloquinoline quinone, derivatives and/or salts thereof in the preparation of drugs for inhibiting the proliferation, oxidative stress status, and migration and invasion of endometrial stromal cells.

In sixth aspect, the present invention relates to the use of pyrroloquinoline quinone, its derivatives and/or salts in combination with antioxidants in the preparation of drugs for inhibiting the proliferation, oxidative stress status, and migration and invasion of endometrial stromal cells.

In seventh aspect, the present invention relates to use in sixth aspect thereof, wherein the said antioxidant is one or more members selected from the group consisting of N-Acetyl-L-cysteine (NAC), resvertrol, Epigallocatechin Gallate (EGCG), Curcumin, Anthocyanidin, Vitamin E or Vitamin C.

In eighth aspect, the present invention relates to use in any one of aspects 1 to 7 thereof characterized in that pyrroloquinoline quinone, derivatives or salts thereof are compounds or salts thereof represented by the following structural formula (I)

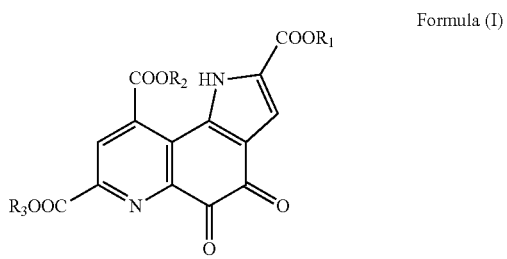

Formula (I)

Wherein R1, R2 and R3 are each independently lower alkyl, lower alkenyl, lower alkynyl, alkaryl, aralkyl, benzyl, H, Na and K.

In ninth aspect, the present invention relates to a drug composition characterized by using the said pyrroloquinoline quinine (PQQ), its derivatives and/or salts in any of aspects of 1 to 8 thereof at effective dose as active ingredients.

In tenth aspect, the present invention relates to the use of drug composition in ninth aspect thereof characterized in that it included one or more members mixed in arbitrary ratio selected from the group consisting of: N-Acetyl-L-cysteine (NAC), resvertrol, epigallocatechin Gallate (EGCG), Curcumin, Anthocyanidin, Vitamin E or Vitamin C.

In eleventh aspect, the present invention relates to the use of drug composition in ninth aspect thereof characterized in that the ratio of pyrroloquinoline quinine, derivatives and/or salts thereof to N-Acetyl-L-cysteine (NAC) is in a range of 1:5 to 1:50.

In twelfth aspect, the present invention relates to the use of drug composition in eleventh aspect thereof characterized in that the daily dose of the said pyrroloquinoline quinine, its derivatives and/or salts is as low as 1 mg/kg/day, and the daily dose of N-Acetyl-L-cysteine is as low as 10 mg/kg/day.

In thirteenth aspect, the present invention relates to the use of drug composition in an eleventh aspect thereof characterized in that the daily dose of the said pyrroloquinoline quinine, its derivatives and/or salts is as low as 0.2 mg/kg/day and the daily dose of N-Acetyl-L-cysteine is as low as 5 mg/kg/day.

In fourteenth aspect, the present invention relates to the use of drug composition in eleventh aspect thereof characterized in that the daily dose of the said pyrroloquinoline quinine, its derivatives and/or salts is within the range of 0.2 to 1 mg/kg/day and the daily dose of N-Acetyl-L-cysteine is in the range of 5 to 10 mg/kg/day.

In fifteenth aspect, the present invention relates to the use of drug composition in eleventh aspect thereof characterized by being applied to pharmaceutical preparations for sustained-release and/or stomach protection.

BRIEF DESCRIPTION OF THE DRAWINGS

FIG. 4-1. Growth curve of endometrial stromal cells treat

FIG. 4-2. Growth curve of endometrial stromal cells treated with 30 uM PQQ in combination with 10 uM NAC.

FIG. 4-3. Growth curve of endometrial stromal cells treated with 3 uM PQQ in combination with 300 nM NAC.

FIG. 4-4. Growth curve of endometrial stromal cells treated with 3 uM PQQ in combination with 30 nM NAC.

FIG. 5. Histogram of the percentage of oxidative free radicals endometrial stromal cells treated with different concentrations of PQQ relative to the controlled group, wherein FIG. 5-1, 5-2, 5-3 represent respectively the relative contents of superoxide anion radical ($O_2.^-$), hydroxyl radical (.OH) and hydrogen peroxide ($H_2O_2$) in the endometrial stromal cells treated with increasing concentrations (0, 30 nM, 300 nM and 3 uM) PQQ (* P<0.05).

FIG. 6-1. Photo of the scratched endometrial stromal cells treated with different concentrations of PQQ.

FIG. 6-2. The statistical curve of the scratch healing test of the scratched endometrial stromal cells treated with different concentrations of PQQ.

FIG. 7-1. Picture of invasive endometrial stromal cells stained with crystal violet after treatment with different concentrations of PQQ.

FIG. 7-2. Statistical histogram of the number of invasive endometrial stromal cells treated with different concentrations of PQQ.

EXAMPLES

Source and Processing of Experimental Compounds

Figure 1:
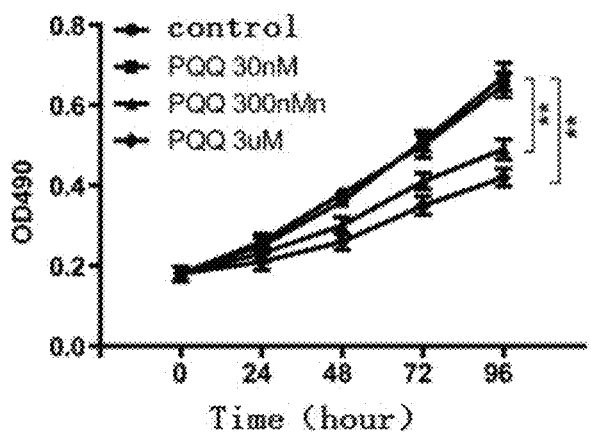
FIG. 1. Growth curve of endometrial stromal cells treated with different concentrations of PQQ.

Unless otherwise specified, PQQ, NAC, resvertrol were purchase from Sigma Company, and were dissolved with double stilled water respectively.

The concentration of mother liquor for PQQ and Resveratrol is 1 mM, The concentration of mother liquor for NAC is 10 mM.

Example 1

PQQ Inhibited Proliferation of Endometrial Stromal Cell in Vitro

Ectopic endometrial tissue primarily consists of epithelial and stromal cells. The ability of proliferation and invasion of these two cells determines the severity of the disease caused by ectopic endometrium. In this Example, the stromal cells in ectopic endometrium were selected to study the inhibitory effect of PQQ on proliferation of endometrial stromal cells in vitro.

Materials and Methods

Isolation of Human Endometrial Stromal Cells

Endometrial tissues were surgically isolated from patients with chocolate cyst of ovary, washed 2 to 3 times with PBS supplemented with antibiotics in ultra-clean cabinet, and cut into tiny pieces (about 1 $mm^3$ in size) with aseptic scissors. The tissues were digested with 1 mg/ml collagenase type I for 30 to 90 min at 37° C., and continually digested with Dnase I (final concentration of 15 U/ml, 2% Dnase I) for another 30 min. The digested tissues were filtered thorough 60-mesh stainless steel filter cell strainer to remove the undigested cell tissues, and were further filtered with 200- or 400-mesh strainer. The filtered solution was centrifuged at 1000 rpm for 5 min. After removing the supernatants, the cells were washed once with culture medium compounded by DMEM/F12 (1:1 v/v) and 10% fetal bovine serum, re-suspended in the culture medium, and seeded in 6-well tissue culture plate or T25 tissue culture flasks with an appropriate density. After 24 hours incubation, the culture medium was changed to remove the non-adherent blood cells, endothelial cells, macrophages and other miscellaneous cells. After primary human endometrial stromal cells were grown to reach 90% confluence, the cells were digested with 0.25% trypsin for 4 to 6 min, and then subcultured with a split ratio of 1:2 to 1:3. Vimentin which expresses specifically in stromal cells was detected by immuno-fluorescence to measure the cell purity. The cells of purity >95% were used in the following experiments.

Determination of Cell Proliferation

Primary ectopic endometrial stromal cells of human were subcultured and the subcultured cells of the 3th to $6^{th}$ passages were chosen as experimental subjects. The cells in logarithmic growth phase were lysed and incubated in the cell culture plate at a density of 50%~60% (i.e. $2\times10^4$ cells/well). After growing adherent on the wall for 24 hours, the cultured cells were divided into groups and each group was given different doses of PQQ. 20 μL MTT (5 mg/ml in PBS, pH=7.4) was added to each well at indicated time points. The cells were incubated in an incubator at 37° C. in a 5% $CO_2$ atmosphere for 4 h. At the end of incubation, the culture supernatant in each cell was carefully aspirated away. 150 μL DMSO was added to each well. Then the wells were shaken with Orbital shaker for 10 min. The absorbance of each cell was detected at wavelength 490 nm. Finally, the cell proliferation curve was drawn.

Detection of Cell Cycle and Apoptosis

Primary ectopic endometrial stromal cells of human were cultured and the subcultured cells of the 3th to $6^{th}$ passages were chosen as experimental subjects. The cells in logarithmic growth phase were lysed and incubated in the cell culture plate at a density of 50%~60% (e.g. $2\times10^4$ cells/well). After growing adherent on the wall for 24 hours, the cultured cells were divided into groups and each group was given different doses of PQQ. 24 h after the drug treatment, the cells were lysed with 0.25% trypsin, and stained the precooled propidium iodide. Cell cycle was determined with flow cytometry. Alternatively, the cells were stained with 5 μL Annexin V-FITC, incubated at 25° C. in the dark for 20 min, stained with 10 μL PI. Cell apoptosis was determined by flow cytometry.

Results:

PQQ Inhibited the Proliferation of Ectopic Endometrial Stromal Cells.

The MTT was used to detect the proliferation of ectopic endometrial stromal cells after treatment with different doses of PQQ. Refer to FIG. 1, the results showed that from 48 h after the drug treatment, PQQ (300 nm and 3 um) can significantly inhibit cell proliferation compared with the control group (p<0.01), while PQQ (30 nm) showed a certain inhibitory effect, but not significant (p>0.05). This indicated that PQQ can effectively inhibit the proliferation of ectopic endometrial stromal cells in a dose-dependant manner.

PQQ Regulated the Cell Cycle of Ectopic Endometrial Stromal Cells.

Figure 2:
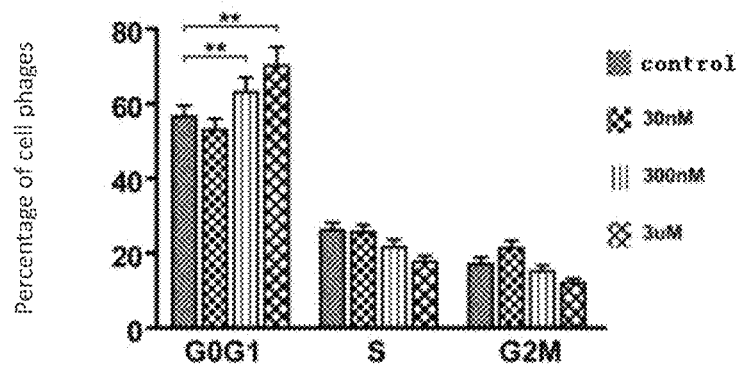
FIG. 2. Histogram of percentage of cells in the different phases of the cell cycle of endometrial stromal cells treated with different concentration of PQQ.

As shown in FIG. 2, the ectopic endometrial stromal cells were treated with different doses of PQQ. The cell proliferation was detected with MTT method (n=6), **p<0.01, which showed that treatment with PQQ (300 nm and 3 um) can arrest the cell in G0/G1 phase (p<0.01). This indicated that PQQ can inhibit the proliferation of ectopic endometrial stromal cells.

PQQ had No Impact on Apoptosis or Necrosis of Endometrial Stromal Cells

Figure 3:
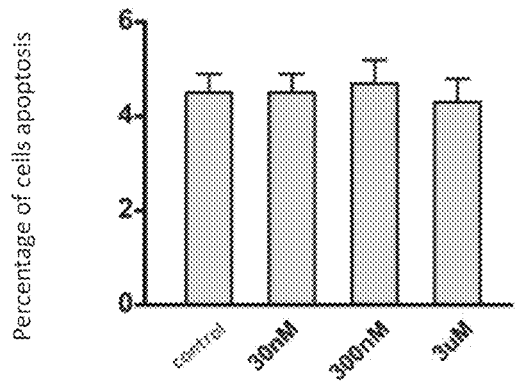
FIG. 3. Histogram of Apoptosis proportion of Endometrial stromal cells treated with different concentration of PQQ.

Refer to FIG. 3, the applicants observed the effects of different concentrations of PQQ on apoptosis of endometrial stromal cells using flow cytometry technique. No endometrial stromal cells apoptosis or necrosis had bee detected compared to the control regardless of dose, indicating that PQQ played its role primarily by regulating cell cycle rather than by a toxic effect, and could not promote cell apoptosis or death.

Example 2

NAC Synergistic with PQQ Inhibited Endometrial Stromal Cell Proliferation

Materials and Methods
Detection of Cell Proliferation

Primary ectopic endometrial stromal cells were cultured and the subcultured cells of the 3th to $6^{th}$ passage were chosen as experimental subjects. The cells in logarithmic growth phase were lysed and incubated in the cell culture plate at a of 50%~60% (e.g. $2 \times 10^4$ cells/well). The cells grew adhering to the wall for 24 hours before being treated with drugs. The cells were divided into groups and each group was given different dose of PQQ. At indicated time point, 20 μL MIT (5 mg/ml in PBS, pH=7.4) was added to every well. The cells were then incubated in an incubator at 37° C. in a 5% $CO_2$ atmosphere for 4 h. After terminating incubation, the culture supernatant in each cell was carefully aspirated away, but formazan crystals should not be aspirated away in any case. 150 μL DMSO was added to each well respectively. All the wells were shaken with Orbital shaker for 10 min to make the crystals adequately solubilized. The absorbance of each cell was detected at wavelength 490 nm. Finally, the cell proliferation curve was drawn.

Result

NAC Inhibited the Proliferation of Ectopic Endometrial Stromal Cells.

According to the report of Charlotte et al. (Ngǒ et al., Am J Pathol. 2009 July; 175(1):225-34.), NAC at a dose of 10 mM can inhibit the proliferation of ectopic endometrial stromal cells. The dose used in mice experiment was 3 g/kg. This means that for an adult with body weight of 50 kg, the corresponding dose will be up to 150 g/day. The applicants deemed that such high dose of PQQ is clinically infeasible. So the applicants investigated the efficacy of PQQ at doses diluted by 1/100 and 1/1000 (i.e. 1.00 uM and 10 uM). The results showed that NAC at a dose of 100 um can effectively inhibit the cell proliferation, while NAC at a dose of 10 um had no evident effect (Refer to FIG. 4).

NAC Synergistic with PQQ Inhibited Endometrial Stromal Cell Proliferation

Figures 1, 4:
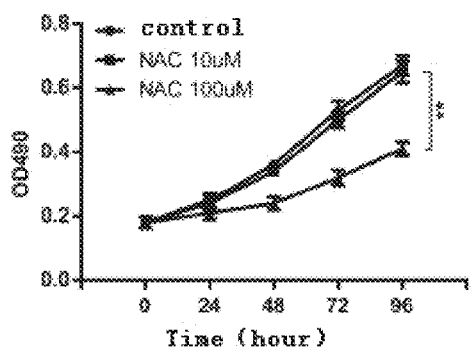
FIG. 4. Growth curve of endometrial stromal cells treated with NAC alone or combined with different concentrations of PQQ.
Figures 2, 4:
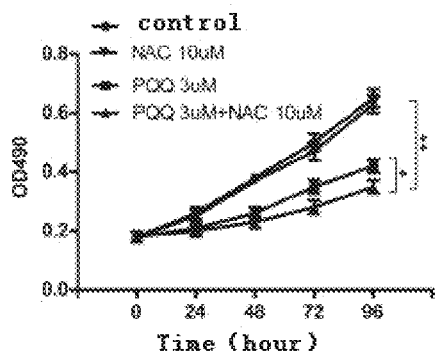
Figures 3, 4:
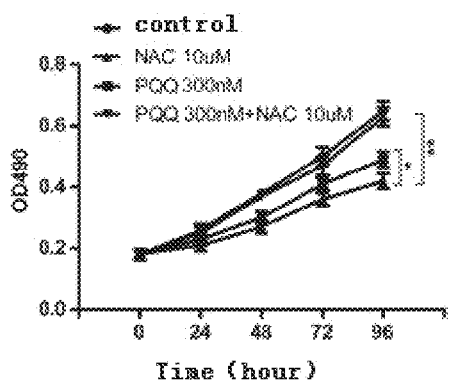
Figure 4:
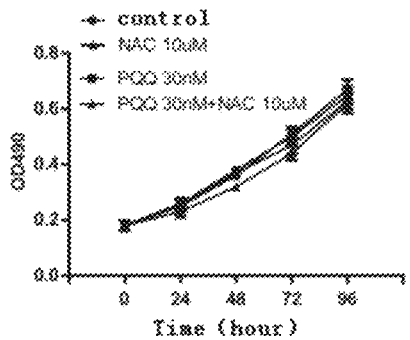
Figures 1, 5:
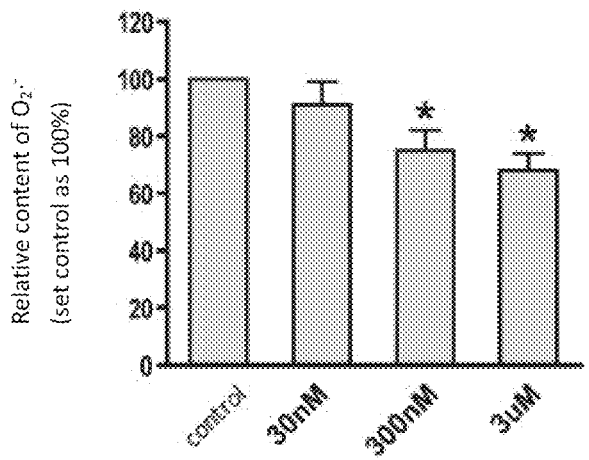
Figures 2, 5:
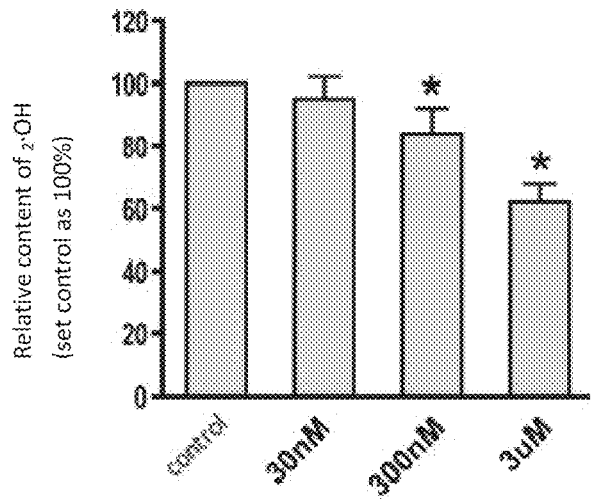
Figures 3, 5:
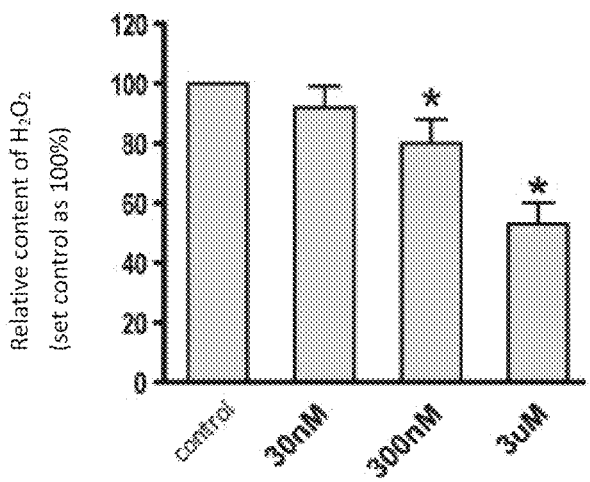

Both NAC and PQQ are of strong reducibility, and similarly can effectively clear oxygen free radicals. In view of the aforesaide, the applicant tried to test whether the combined use of the two compounds could produce synergistic effects. The detailed experimental procedure is as follows: use 10 uM NAC, which is ineffective when used alone in cell experiment, in combination with PQQ at three different doses, 30 nM, 300 nM and 3 uM respectively; Test the effect of the three combinations on the cell proliferation with MTT technique. The result showed that 3 uM PQQ in combination with 10 uM NAC can significantly inhibit the cell proliferation ($p<0.01$) with efficacy better than PQQ used alone ($p<0.05$), as shown in FIG. 4-2. 300 nM PQQ in combination with 10 uM NAC can significantly inhibit the cell proliferation ($p<0.01$), with efficacy better than 300 nM PQQ used alone ($p<0.05$), as shown in FIG. 4-3. In contrast, 30 nM PQQ in combination with 10 uM showed no significant effects, as shown FIG. 4-4.

Example 3

PQQ Inhibits Oxidative Stress Status in Endometrial Stromal Cells

Materials and Methods

Superoxide anion ($O_2.^-$) assay kit was purchased from Nanjing Jiancheng Bioengineering Insitute; Hydroxyl free radical assay kit was purchased from Shanghai Xinyu Biological Technology Co., Ltd., Hydrogen Peroxide Assay Kit was purchased from Beyotime Biotechnology Research Institute.

Determination of Superoxide Anion ($O_2.^-$) Content

The cells were cultured in 96-well cell culture plates for 24 h after the cells adhered to the plate. Three different concentrations PQQ (30 nm, 300 nm and 3 um) were added to the culture medium respectively. After additional 18 h incubation, the culture medium was discarded, and fresh culture medium supplemented with NBT (a final concentration of 1 mg/mL) was added to the cells. The cells were continually cultured for another 1 h at 37° C. The cells were fixed with 100% methanol, and naturally dried. 120 μL KOH (2 mol/L) and 140 μL DMSO were added to the cells. The optical density at wavelength 570 nm was measured.

Determination of Hydrogen Peroxide ($H_2O_2$) Content

The cells were seeded in 6-well cell culture plates and incubated for 24 h after the cells adhered to the plate. Three different concentrations PQQ (30 nm, 300 nm and 3 μm) were added to the cultures respectively. After additional 18 h incubation, the cells were lysed using the lysis buffer contained in reagent kit, centrifuged at 12000×g for 5 min at 4° C. 50 μL of sample supernatant was mixed with 100 μL detection solution, rested 30 min at room temperature. The optical density at wavelength 560 nm was measured.

Determination of Hydrogen Radical (.OH) Content

The cells were seeded in 6-well plate at $8 \times 10^5$ cells/well, and incubated for 24 h after the cells adhered to the plate. Three different concentrations of PQQ (30 nm, 300 nm and 3 μm) were added to the cultures respectively. The cells were incubated for additional 18 h. At the end of the treatment, the cultured cells were collected. 50 μL samples were added to each cell, followed by addition of 50 μL of antibody working solution. The sample was shaken to achieve a uniform mixture, and reacted at 37° C. for 30 min. The plates were then washed for four to five times. 100 μL of enzyme marker was added to each well. The resulting mixture was allowed to react for 20 min at 37° C. Coloration method: 50 μL of buffer liquid and 50 μL of substrate solution were added to each well in sequence. The mixture solution was gently shaken to achieve a uniform mixing, and coloured for 10 min in the dark at 37° C. Measurement method: After adding 50 μL of termination solution to each cell, the mixture solution was gently shaken until it was mixed uniformly. The optical density at wavelength 560 nm was measured with microplate reader (Read the data in 20 min).

Results:

PQQ cleared the reactive oxygen species in endometrial stromal cells Oxygen free radical include superoxide anion radical ($O_2.^-$), hydroxyl radical (.OH), hydroperoxyl radical (HOO.) and Lipid peroxide radical (ROO.) and so on. They together with singlet oxygen ($^1O_2$), hydrogen peroxide ($H_2O_2$), ozone ($O_3$) are generally called reactive oxygen species (ROS). FIG. 5-1, 5-2, 5-3 showed the relative content of superoxide anion radical ($O_2.^-$), hydroxyl radical (.OH) and hydrogen peroxide ($H_2O_2$) in endometrial stromal cells treated with increasing concentration of PQQ (0, 30 nM, 300 nM and 3 μM). The results demonstrated that the relative concentrations of the three ROS all significantly declined in endometrial stromal cells treated 300 nM and 3 uM PQQ. This indicated that PQQ can clear ROS in endometrial stromal cells, thereby performing antioxygen free radical function in endometrial stromal cells.

Example 4

PQQ Inhibited the Migration and Invasion of Endometrial Stromal Cells

Background

EM is a benign disease with low canceration rate, but its biological behaviour extremely resembles that of malignant tumours. Especially, it has the ability of invading tissues and distant planting as malignant tumours. Ectopic endometrium invades the pelvic cavity, peritoneal cavity, peritoneum or other organ surfaces by adhesion. The degradation of the attached extracellular matrix (ECM) barrier is a necessary condition for its planting and growth.

Degradation of ECM mainly depends on the role of proteolytic enzymes. Matrix metalloproteinases (MMPs) are one group of the most important proteolytic enzymes, which can degrade almost all components of ECM, and play a crucial role at the degradation and reconstruction of ECM and basement membrane. Tissue inhibitors of matrix metalloproteinases (TIMP) are the natural, specific inhibitor of MMP. MMP/TIMP imbalance is of great significance in the pathogenesis of endometriosis. The research by Uzan et. al. (Uzan et. al., B1, Virchows Arch. 2004 December; 445(6): 603-9) showed that the activity of MMP and TIMP in ectopic endometrium was altered. Specifically, the expression of MMP-1, -2, -3, -7, -9 and -11 increased, while the expression of TIMP-1, -2 and -3 decreased, leading to MMP/TIMP imbalance. The imbalance promoted degradation of ECM and increased invasive ability of ectopic endometrium (Jana et. al., Indian J Biochem Biophys. 2012 October; 49(5): 342-8). Inhibiting MMP by various means can alleviate the development of EM to a certain extent.

Materials and Methods

Scratch Test:

Before the cells were plated, horizontal lines were scratched on the back of 24-well plate using a blade with the guide of a ruler. For each well, three evenly distributed lines which horizontally crossed the well were scratched. Two days after transfection, the cell fusion rate reached 90%. The wound were created by scratching on the cell layer with micropipette tip in a direction perpendicular to the lines on the back of the plate with the aid of ruler. During the operation, the micropipette tip should be kept perpendicular to the plate, and not tilt to one side. The cells were washed for three times with PBS to remove the exfoliated cells after being scratched, and 1640 culture medium supplemented with 2% FBS was added to the cells. The cells were cultured in an incubator at 37° C., in an air atmosphere containing 5% $CO_2$. The cells were photographed in the same field of view at each indicated time point.

Transwell Assay:

500 µL culture medium containing 10% FBS was added into each wells in a 24-well plate. Transwell chambers were treated with 0.3 mg/ml FN diluted by serum free 1640 culture medium (BD company). The cells were seeded ($5\times10^4$ cells/chamber) in the transwell up-chamber, in which 100 µL media were kept finally. The cells were cultured in an incubator at 37° C. in an air atmosphere containing 5% $CO_2$ for the specified time. The chambers were taken out, stained with 0.1% crystal violet, and were photographed. Crystal violet on the membrane was dissolved with 300 µL of 33% Glacial acetic acid. The optical absorption was measured at wavelength 573 nm.

Matrigel Invasion Assay

On the ice, 100 µL matrigel was taken in with pre-chilled micropipette, transferred into 300 ul pre-chilled serum free medium. The mixture solution was thoroughly mixed to achieve uniform. 25 ul of the previous diluted matrigel was put into transwell up-chamber, covering the whole carbon ester membrane. The transwell was incubated at 37° C., 30 min for Matrigel gelling. The rest treatment was the same as that in Transwell assay.

Results

Treatment with PQQ Restrained the Migration of Cells

Figures 1, 6:
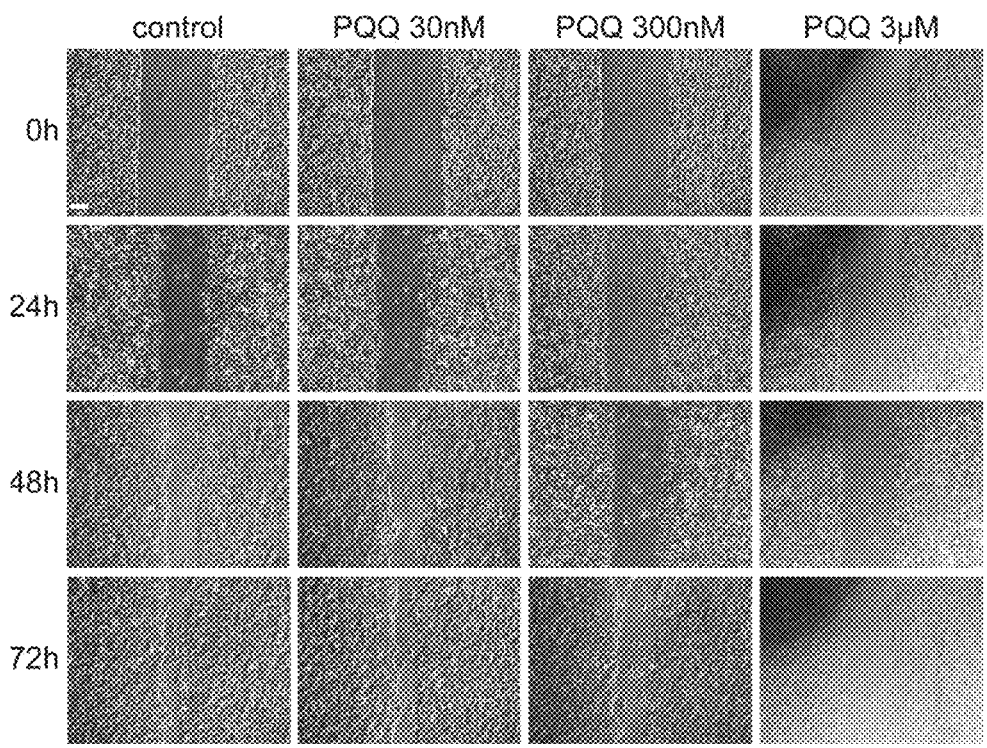
Figures 2, 6:
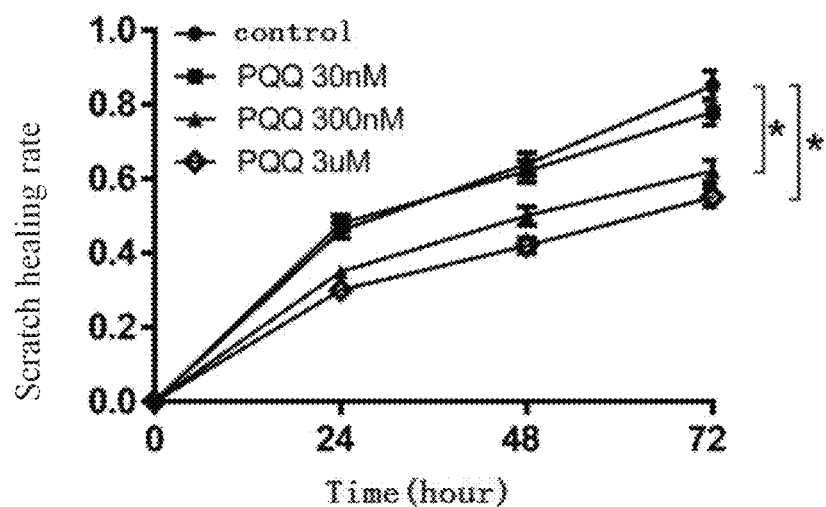

Refer to FIGS. 6-1 and 6-2, scratch healing experiments showed that endometrial cells covered 85% of the scratch area in 72 h. 30 nM PQQ could partially restrain the migration of the endometrial cells, but was statistically meaningless (P>0.05). However the group treated with 300 nM PQQ showed certain difference with the control group at 24 h, the inhibition effect of cell migration become more evident at 48 h and 72 h (P<0.05). The inhibition effect of the group treated with 3 µM PQQ is the most evident, at 72 h its scratch coverage rate was 42% lower than that in the control group. In conclusion, PQQ at concentrations of 300 nM and 3 µM can significantly inhibit scratch healing (P<0.05).

PQQ Inhibited Invasion of Endometrial Stromal Cells

Figures 1, 7:
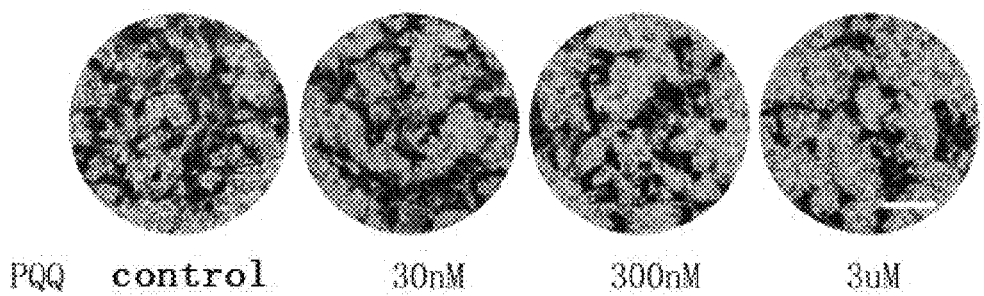
Figures 2, 7:
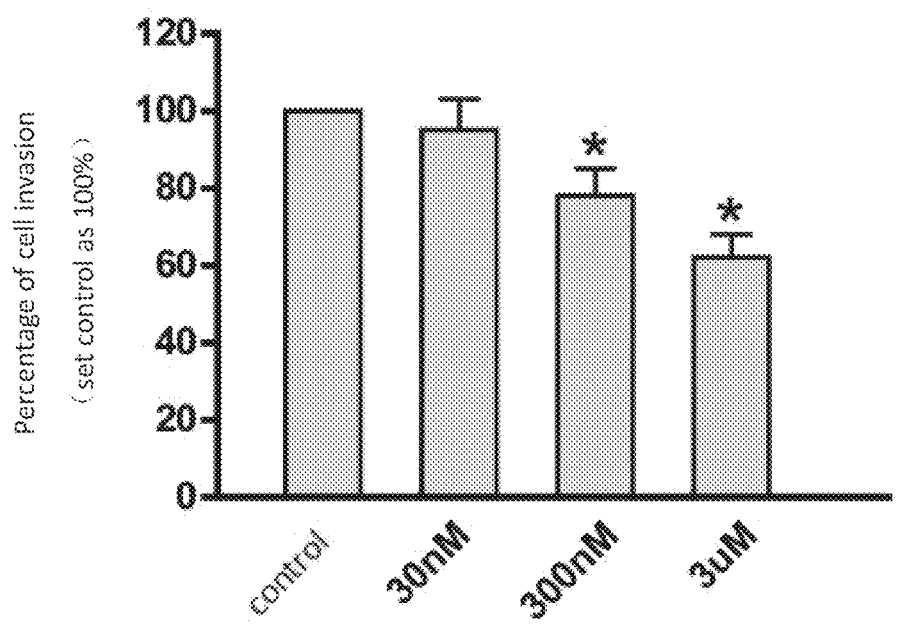

Refer to FIGS. 7-2 and 7-3, the transwell/matrigel invasion assay showed that: as compared to the control group, at 48 h the inhibitory effect on cell invasion of 30 mm PQQ was not obvious, while 300 nM PQQ showed definite inhibitory effect, which was statistically meaningful. Treatment with 3 µM PQQ reduced the invasion ability of endometrial stromal cells by 35%. In conclusion, PQQ at concentrations of 300 nM and 3 µM can significantly inhibit the endometrial stromal cells (P<0.05).

Example 5

PQQ Inhibited Endometriosis Foci in Rats

Materials and Method:

Establishment of Endometriosis Rat Model

Animals were healthy female SD rats with a mass from 200 g to 220 g of clean grade, which were provided by Shanghai Slac Experimental Animal Co. Ltd. (animal certification number was SCXK(Hu)2007-0005). After routine disinfection of rats' skin, a midline median incision about 2 cm long was performed in the lower abdomen. The uterus was found at the back of the bladder. The left uterus was dissociated, and its proximal part was ligated at 1 cm from the left uterine horn, and the distal part was ligated at 1 cm from the ovary. The cut uterus tissue was placed in a Petri dish containing sterile saline. The uterus was opened longitudinally, and a piece of endometrial tissue (4 mm×4 mm) was cut. A tunnel was created between the abdominal muscle and the subcutaneous fascial layer on the right side of the abdominal incision, with appropriate size for the placement of the endometrium. The endometrial tissue was placed flat at the bottom of the tunnel, making the lining of endometrium closely attached to the abdominal muscles, and then the incision was closed routinely. The rats were injected with Penicillin (400 KU/rat) for 3 days after operation and fed normally. The intramuscular injection of estradiol (0.1 mg·kg·d) was performed since the next day after the operation, once every 4 days for 3 times to promote ectopic endometrial growth. After the operation, the lump was touched twice a week to observe the mass and size of the lump. On the 21th day, the lump could be evidently observed. Measure the lump size with vernier calliper, calculate the volume of the lump by multiplying the long diameter with short diameter's square and divided by 2. The rats with lump larger than 60 mm$^3$ were considered as qualified model.

Experimental Grouping

A total of 54 qualified rats were divided into 6 groups randomly and treated with drug since the 22th days (total 4 weeks). The groups were divided as follows:

TABLE 1

Rats grouping table

| Group | Number | Drug dose | Administration route | Duration |
|---|---|---|---|---|
| Control group | 9 | PBS | Water feeding | 4 week |
| PQQ group | 9 | PQQ (1 mg/kg) | Water feeding | 4 week |
| NAC group | 9 | NAC (10 mg/kg) | Water feeding | 4 week |
| Res group | 9 | Resveratro (10 mg/kg) | Water feeding | 4 week |
| PQQ + NAC group | 9 | PQQ(1 mg/kg) NAC (10 mg/kg) | Water feeding | 4 week |
| PQQ + Res group | 9 | PQQ(1 mg/kg) Resveratro (10 mg/kg) | Water feeding | 4 week |

Determination of the Weight of Transplanted Foci

After feeding the drugs for 4 weeks, the rats were anesthetized. The transplanted foci was surgically removed and weighed.

Results:

Model Creation

A total of 63 SD rats were used, and 54 of them showed small cysts at the graft. In 7 cases, the masses of lump did not reach the required volume. The possible reason for the failure was that the endometrial area is too small or that the lining of endometrium was not thoroughly separated from the muscular layer. Two of the rats died from accidents.

The Curative Effect of PQQ on Endometriosis

After 4 weeks treatment, comparison of the volume of ectopic endometrial foci among each experimental group showed that the weight of ectopic endometrial foci from groups of PQQ, PQQ+NAC, PQQ+Res were evidently lower than that from the control group, with statistically meaningful difference, while in the group of NAC or Res alone, the volume of ectopic endometrial foci showed no evident difference from that of the control group. Combination of PQQ with NAC, Resveratro showed a better efficacy than PQQ alone (P<0.01), indicating that PQQ has a synergistic effect with these antioxidants.

TABLE 2

Comparison of the weight of ectopic endometrial foci after treatment of endometriosis in rats model

| Group | Number | weight of cysts after treatment (mg) Mean ± SD |
|---|---|---|
| Control group | 9 | 145.2 ± 42.8 |
| PQQ group | 9 | 71.2 ± 23.2*# |
| NAC group | 9 | 138.1 ± 33.1 |
| Res group | 9 | 122.1 ± 30.7 |
| PQQ + NAC group | 9 | 42.3 ± 14.3* |
| PQQ + Res group | 9 | 49.8 ± 17.8* |

Note:
*denotes comparison between individual group and the control group (P < 0.01),
donotes comparison between PQQ and PQQ + NAC groups, PQQ and PQQ + Res groups respectively(P < 0.01).

Example 6

PQQ Inhibited Endometrial Stromal and Glandular Infiltration in Adenomyosis Mouse Model Materials and Method Disodium salt of PQQ was used in the present experiment (PQQ-Na$_2$, donated by MITSUBISHI gas chemical (MGC), Japan). The salt was dissolved with water and the concentration of its mother liquid is 1 mg/mL.

In the present Example, the mouse model of adenomyosis was created with tamoxifen. This method is easy to operate, the rate of molding can reach 100%, and the difference between the model mouses caused by the operation is small. At 2~5 days after birth (the birth day was the first day), the mice were fed with 5 ul/(g·BW) peanut oil/lecithin/condensed milk mixture (volume ratio 2:0.2:3) supplemented with 0.2 mg/ml tamoxifen (produced by shanghai Fudan Fuhua Pharmaceutical Co, Ltd.) by drip feeding. In the negative control group, the mice were fed with peanut oil/lecithin/condensed milk mixture (volume ratio 2:0.2:3), with no tamoxifen added. All the mice were exposed to light for 12 h/day, and were reared by maternal lactation during 1-21 days of age. After 22 days of birth, the mice were separated with mother mice, and the female mice were reserved for the next experiment.

After 3 months, 7 model mice were killed after anesthesia. Pathological section analysis of endometrial tissue invasion of muscle layer proved that all the mice had suffered from the disease. The remaining model mice were divided into 5 groups with 20 mice in each group. One of the groups was chosen as model control group (fed with normal water). The drinking water for other group were supplemented with PQQ (1 mg/kg/day), NAC (10 mg/kg/day), PQQ (1 mg/kg/day) +NAC (10 mg/kg/day) (denoted by P+N (H)); PQQ (0.2 mg/kg/day) +NAC (5 mg/kg/day) (denoted by P+N (L)).

After treatment with drugs for 4 weeks, the mice were killed by anesthesia. The uterus was surgically removed and the invasion of endometria into myometrium was analyzed by the pathological section.

Figure 8:
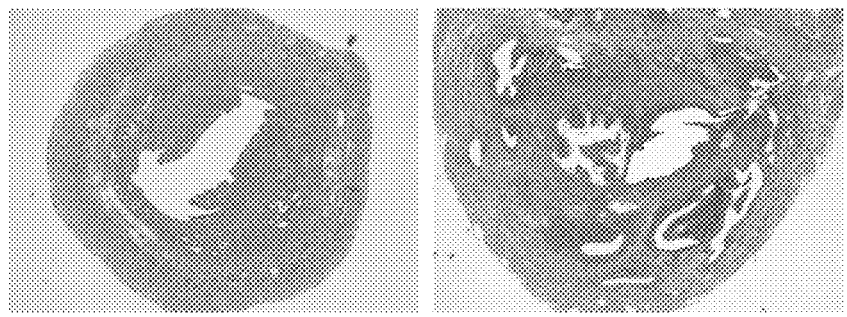
FIG. 8. Pathological section of uterus in model group (left) and control group (right) of adenomyosis.

The results were shown in FIG. 8. In the case of the negative control group, the uterus was well organized with clear layers of endometrium, muscularis, and serosa. No stromal and glandular tissue was found to invade the muscularis layer. In the case of model control group, the structure of intima and muscle layer is disordered, and invasion of intimal stromal into muscularis can be obviously seen. The muscular layer was divided into cords, and the endometrial gland could be seen in the muscularis layer.

In the 20 mice of the model control group, the stroma and glands were found to invade the muscularis, and the incidence of adenomyosis was 100%. The statistical data of incidence of adenomyos in the other groups was listed in table 3.

After 4 weeks treatment, comparison of the infiltration of endometrial stroma and glands among the experimental groups showed that in the groups of PQQ, P+N (H), P+N (L), the number of rice with the infiltration of endometrial stroma and glands were evidently lower than that in the model control group, with statistically meaningful difference (P<0.05), indicating that PQQ either alone or in combination with NAC had obvious curative effect on adenomyosis. The group treated with NAC alone showed no obvious difference with the control group. Combination of PQQ and NAC showed better curative effect than PQQ alone, in both high concentration group (H) and low concentration group (L). This indicated that PQQ has a synergistic effect with NAC antioxidants

TABLE 3 comparison of the infiltration of endometrial stroma and glands in rats

| group | infiltration of endometrial stroma positive animals/total animals | infiltration of endometrial glands positive animals/total animals |
|---|---|---|
| Model control group | 20/20 | 20/20 |
| PQQ group | 10/20*# | 9/20*# |
| NAC group | 19/20 | 18/20 |
| P + N (H) group | 2/20* | 1/20* |
| P + N (L) group | 2/20* | 2/20* |

Note:
*denotes comparison between individual group and control group (P < 0.05).
denotes comparison between PQQ group and P + N (H), PQQ and P + N (L) (P < 0.05).

Example 7

Disodium Salt of PQQ Inhibited Endometriosis Foci in Rat Materials and Method

Disodium salt of PQQ was used in the present experiment (PQQ-$Na_2$, donated by MITSUBISHI gas chemical (MGC), Japan). The salt was dissolved with water and the concentration of its mother liquid is 1 mg/mL.

Refer to Example 5 for the method for creating endometriosis rat model. 60 qualified model rat were divided into 5 groups with 12 in each group. One of the groups was chosen as model control group (fed with normal water). The drinking water for other group were supplemented with PQQ (1 mg/kg/day), NAC (10 mg/kg/day), PQQ (1 mg/kg/day)+NAC (10 mg/kg/day) (denoted by P+N (H)); PQQ (0.2 mg/kg/day)+NAC (5 mg/kg/day) (denoted by P+N (L)).

Results:

Model Creation

A total of 77 SD rats were used, and 61 of them showed evident small cysts at the graft with the volume meeting the experimental requirement. 60 qualified model rats were chosen and randomly divided into 5 groups.

The Curative Effect of PQQ on Endometriosis

After 4 weeks treatment, comparison of the volume of endometrial foci among the experimental groups showed that in the groups of PQQ, P+N (L), P+N (H), the weight of ectopic cyst was evidently lower than that in the model control group, with statistically meaningful difference (P<0.05). This indicated that PQQ either alone or in combination with NAC could significantly inhibited the growth of endometrial ectopic foci. The group treated with NAC alone showed no obvious difference with the control group. Combination of PQQ and NAC showed better curative effect than PQQ alone, in both high concentration group (H) and low concentration group (H) (P<0.01). This indicated that PQQ has a synergistic effect with NAC antioxidants.

TABLE 4

Comparison of the weight of ectopic cyst between the treated with disodium salt of PQQ and the group treated with combination disodium salt of PQQ and NAC.

| Group | Number | weight of ectopic cys after treatment (mg) Mean ± SD |
|---|---|---|
| Control group | 12 | 152.6 ± 15.3 |
| PQQ group | 12 | 69.5 ± 12.7*# |
| NAC group | 12 | 142.1 ± 13.4 |
| P + N(H) group | 12 | 32.1 ± 10.1* |
| P + N(L) group | 12 | 43.4 ± 8.9* |

Note:
*denotes comparison between individual group and control group (P < 0.05).
denotes comparison between PQQ group and P + N (H), PQQ group and P + N (L) (P < 0.05)

The above experiments demonstrated that:

PQQ can significantly inhibit the proliferation and cell cycle of endometrial stromal cells; can inhibit endometrial stromal cell invasion. Treatment with PQQ can inhibited the oxidation stress status of endometrial stromal cells in a dose-dependent fashion; Use of PQQ in combination with NAC has a synergistic effect on inhibition of cell proliferation was obvious: inhibit the proliferation of endometrial stromal cells in vitro. In vivo, the proposed treatment can significantly reduce the size of endometriotic lesions, significantly reduced infiltration of endometrial stroma and glands, and significantly reduce the dosage of NAC agent. Both PQQ and PQQ in combination with NAC have obvious therapeutic effects on adenomyosis. Therefore, the PQQ or PQQ in combination with NAC as a drug will create a new approach for the treatment of endometriosis with no side effects, especially in that the treatment does not interfere with pregnancy.

The dose of PQQ in rats used in the present invention was 1 mg/kg body weight/day, which can effectively inhibit the proliferation of endometrial foci. When applied to human body, this dose is comparable to the recommended amount of PQQ as a health care product, thus being completely safe. In the past, in the experimental study of treating endometriosis in animals with NAC, the effective dose is 1.3/kg body weight/day. This dose is too high to be applied to human body.

The dose of NAC that the applicants used in the present experiments is only 1 percent of that previously used in animal experiments. NAC alone showed no evident curative effect. However, the combination of PQQ with NAC at this dose showed evident synergistic effect. The size of ectopic endometrial foci treated with this drug combination was 59% of that treated with PQQ alone, 34% of that in the control group. The involvement of PQQ can significantly reduce the dose of NAC. Meanwhile, the efficacy was improved by 100%.

In the adenomyosis model, the synergistic effects of the two compounds were also very significant. Combination of PQQ and NAC showed better curative effect than PQQ alone (P<0.01), in both high concentration group (H) and low concentration group (H). This indicated that there existed a synergistic effect between PQQ and NAC antioxidants. NAC is similar to PQQ in that both of them can effectively clear oxygen free radicals in tissues. But the stabilities of them are very different, and may play a different role in different antioxidation segment, thus showed good synergistic effects, implying that the combination of PQQ and NAC has good prospects in clinical applications.

Resveratrol is a kind of polyphenolic compound, which is mainly from grapes (red wine), Polygonum cuspidatum, peanuts, mulberry and other plants and is a strong antioxidant. Epigallocatechin-3-gallate (EGCG) is a catechin monomer isolated from tea leaves, and is the main component of the biological activity of tea polyphenols. EGCG has very strong antioxidant activity. Ricci et. al. (HumReprod, 2013 January; 28 (1):178-88) reported that EGCG and Resveratrol both can effectively inhibit the lesion of EM model mice by antioxidation effect.

According to the experimental study of the applicants, PQQ in combination with EGCG, Resveratrol, Vitamin E or C can all significantly reduce the damaged size of endometriosis.

Human Dose and Dosage Forms

Dose of PQQ:

In the present invention, the dose of PQQ used in animal experiment is 0.2-1 mg/kg/day. This dose is commonly used in animal experiments, corresponding to about 12-60 mg/day for adults. Taking into account the difference in metabolic rates between humans and mice, this dose is approximately 2-20 mg/per day for adults (The assumed adult body weight was 60 kg, the same as below).

Dose of NAC and Resveratrol

In the present invention, the dose of NAC or Resveratrol used in animal experiment was 5-10 mg/kg/day. This dose corresponded to about 300-600 mg/day for adults. Taking into account the difference in metabolic rates between humans and mice, this dose is approximately 50-200 mg/per day for adults, which is only 1/10-1/40 of the dose used in the experiment of treating EM in human body with NAC, as mentioned in the previous background section.

As described above, in accordance with the teachings of the present invention, the general technical personnel in the field can comprehend the dosage mentioned above refers to the therapeutic effective amount, i.e. a dose that can effectively treat and/or prevent endometriosis described in the present invention such as adenomyosis, ovarian chocolate cysts, and deep invasive endometriosis, or a dose that can effectively inhibit endometrial stromal cell proliferation, oxidative stress and migration and invasion including the dose of PQQ as active ingredient, as well as the total dose of PQQ combined with NAC or other agents as active ingredient and the dose of individual agent thereof. By reading the invention, the technical personnel in the field can learn that the effective dose of the invention is an important part of the invention and compose the present invention together with the other parts of the invention.

Pharmaceutical Preparations

The pharmaceutical composition of the present invention can be prepared in a manner known to the technical personnel in the pharmaceutical field. The composition may contain an amount of therapeutically effective amount of PQQ, or a combination of therapeutically effective amounts of PQQ and NAC or other substances, and an appropriate carrier or excipient of a carrier or medium of an active ingredient, according to the present invention. The said carrier or excipient is known in the field. The pharmaceutical composition is preferably suitable for oral administration. The compositions can be administered in different forms, preferably in tablet form. Other forms, such as capsules, suppositories, solutions, suspensions, syrups, etc., are also possible. Many different slow-release techniques and preparations are known in this field and can be applied to the present invention. Formulations with a combination of slow-release and gastric protection are also possible and can be used in the present invention.

What is claimed is:

1. A method of treating endometriosis, which comprises:
administering a pharmaceutically effective amount of a drug to a subject in need thereof, wherein the drug comprises:
(a) pyrroloquinoline quinine (PQQ) or a disodium salt thereof of the following formula:

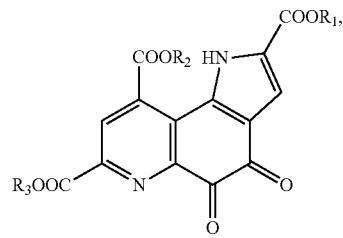

wherein $R_1$, $R_2$ and $R_3$ are each selected from a group consisting of alkenyl, lower alkynyl, alkaryl, aralkyl, phenyl, H, Na and K, in an amount of 0.2 to 1 mg/day per kg of a weight of the subject, and
(b) N-acetyl-L-cysteine (NAC) in an amount of 5 to 10 mg/day per kg of a weight of the subject;
wherein a molar ratio of PQQ or salt thereof to NAC is 1:33 to 1:50, and wherein the subject is a mammal with endometriosis, or cells, or tissues of the mammal.

2. The method of claim 1, characterized in that said endometriosis is chocolate cyst of ovary.

3. The method of claim 1, characterized in that said endometriosis is deeply infiltrating endometriosis.

* * * * *